United States Patent
Hartmann et al.

(10) Patent No.: US 6,799,068 B1
(45) Date of Patent: Sep. 28, 2004

(54) METHOD FOR VERIFYING THE CALCULATED RADIATION DOSE OF AN ION BEAM THERAPY SYSTEM

(75) Inventors: Gunther Hartmann, Darmstadt (DE); Oliver Jaekel, Darmstadt (DE); Peter Heeg, Darmstadt (DE); Christian Karger, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 0 days.

(21) Appl. No.: 09/890,896
(22) PCT Filed: Feb. 8, 2000
(86) PCT No.: PCT/EP00/00994
§ 371 (c)(1), (2), (4) Date: Nov. 13, 2001
(87) PCT Pub. No.: WO00/48679
PCT Pub. Date: Aug. 24, 2000

(30) Foreign Application Priority Data

Feb. 19, 1999 (DE) .......................................... 199 07 774

(51) Int. Cl.[7] ............................................... A61N 1/00
(52) U.S. Cl. ........................................................ 607/2
(58) Field of Search ............................. 250/251, 252.1, 250/492.1, 492.3, 306, 307, 492.21, 505.1; 128/898; 607/2, 3; 600/436; 315/501, 505

(56) References Cited

U.S. PATENT DOCUMENTS

| | | | | |
|---|---|---|---|---|
| 5,813,985 A | * | 9/1998 | Carroll ........................ | 600/436 |
| 6,600,164 B1 | * | 7/2003 | Badura et al. ............ | 250/492.3 |
| 6,614,038 B1 | * | 9/2003 | Brand et al. .............. | 250/492.3 |

* cited by examiner

Primary Examiner—George Manuel
(74) Attorney, Agent, or Firm—Frommer Lawrence & Haug LLP; Ronald R. Santucci (57) ABSTRACT

A method for the verification of the calculated radiation dose of an ion beam therapy system that comprises a grid scanner device, arranged in a beam guidance system (6, 8), having vertical deflection means (13) and horizontal deflection means (14) for the vertical and horizontal deflection of a treatment beam (11) perpendicular to its beam direction, with the result that the treatment beam (11) is deflected by the grid scanner device to an isocentre (10) of the irradiation site and scans a specific area surrounding the isocentre (10), irradiation being carried out on the basis of automatically calculated radiation dose data. The accuracy of the calculation of the radiation dose data is verified by using a phantom, a discrepancy between the radiation dose calculated for the at least one measurement point of the phantom and a radiation dose measured for the at least one measurement point being determined and evaluated.

13 Claims, 4 Drawing Sheets

METHOD FOR VERIFYING THE CALCULATED RADIATION DOSE OF AN ION BEAM THERAPY SYSTEM

The present invention relates to a method for the verification of the calculated radiation dose of an ion beam therapy system especially operated with heavy ions.

Ion beam therapy systems are preferably used in the treatment of tumours. An advantage of such systems is that, on irradiation of a target object (target), the major portion of the energy of the ion beam is transferred to the target, while only a small amount of energy is transferred to healthy tissue. A relatively high dose of radiation can therefore be used to treat a patient. X-rays, on the other hand, transfer their energy equally to the target and to healthy tissue, so that for health reasons, for the protection of the patient, it is not possible to use a high dose of radiation.

There is known from U.S. Pat. No. 4,870,287, for example, an ion beam therapy system in which there are generated from a proton source proton beams of which the protons can be delivered to various treatment or irradiation sites by an accelerator device. Provided at each treatment site is a rotating cradle having a patient couch so that the patient can be irradiated with the proton beam at different angles of irradiation. While the patient is spatially located in a fixed position inside the rotating cradle, the rotating cradle revolves round the body of the patient in order to focus the treatment beams at various angles of irradiation onto the target located in the isocentre of the rotating cradle. The accelerator device comprises a combination of a linear accelerator (LINAC) and a so-called synchrotron ring.

In H. F. Weehuizen et al. CLOSED LOOP CONTROL OF A CYCLOTRON BEAM FOR PROTON THERAPY, KEK Proceedings 97–17. January 1998, a method of stabilising the proton beam in proton beam therapy systems is proposed in which the treatment beam is actively so controlled that it is located on the centre line of the corresponding beam delivery system at two measurement points spaced from each other in the longitudinal direction. The first measurement point is located between a pair of deflection magnets and is formed by a multi-wire ionisation chamber. Depending on the actual value of the beam position delivered from that multi-wire ionisation chamber relative to the centre point of the beam path, a PI control is generated by further deflection magnets arranged upstream from the first-mentioned pair of deflection magnets. The second measurement point is located just upstream of the isocentre and is formed by an ionisation chamber which is divided into four quadrants. Depending on the actual position value of that ionisation chamber, again PI control signals are generated, but those control signals are intended for the first-mentioned deflection magnets. Such a control arrangement is said to render possible both angle stability in terms of the centre line of the beam delivery system and lateral position stability of the proton beam.

When, however, heavy ion irradiation is carried out, that is to say irradiation with ions that are heavier than protons, large and heavy devices are necessary, with the result that there is a tendency to avoid the use of rotating cradles and instead move the patient or the patient couch. Corresponding therapy systems are described, for example, in E. Pedroni: Beam Delivery, Proc. 1$^{st}$ Int. Symposium on Hadrontherapy, Como, Italy, Oct. 18–21, 1993, page 434. Such systems are accordingly eccentric systems.

Since, however, mainly isocentric systems are preferred by oncologists, a heavy ion beam therapy system was proposed in which, although rotating cradles are used at the treatment sites, the radii of the rotating cradles can be reduced by virtue of the treatment beam delivered to each rotating cradle horizontally along its axis of rotation being so guided by means of suitable magnet and optics arrangements that, for the irradiation of a target, the beam is first of all directed away from the axis of rotation and later crosses the axis of rotation again in the isocentre. There is provided for the irradiation of the target a grid scanner, which comprises vertical deflection means and horizontal deflection means, each of which deflects the treatment beams perpendicular to the beam axis, with the result that an area surrounding the target is scanned by the treatment beams. Such a system thus essentially provides beam guidance in only one plane of the rotating cradle.

The irradiation by the grid scanner is carried out with the aid of radiation dose data, which are automatically calculated by the supervisory control system of the ion beam therapy system in dependence upon the patient to be irradiated or treated.

Since a high level of operational safety and operational stability in terms of the treatment beam is always necessary in ion beam therapy systems, a monitoring device for monitoring the treatment beam delivered by the grid scanner is provided in the afore-described heavy ion beam therapy system. This monitoring device is arranged between the last deflection magnet of the above-mentioned magnet arrangement and the isocentre, and can comprise ionisation chambers for monitoring the particle flow and multi-wire chambers for monitoring the beam position and the beam width.

For safety reasons, various DIN standards have to be observed in the operation of medical electron accelerators. Those standards are concerned on the one hand with the inspection test, that is, the inspection of the readiness for operation, and on the other-hand with the consistency test, that is, examination of operational stability, of the system. For ion beam therapy systems, especially for heavy ion beam therapy systems, safety standards of that kind developed specifically for such systems are not yet known, but there is still a need, in ion beam therapy systems too, for as high as possible a level of operational safety and operational stability.

The problem underlying the present invention is therefore to propose a method for the verification of the calculated radiation dose of an ion beam therapy system in order to improve the operational safety and operational stability, especially in respect of the irradiation planning. The method shall at the same time be suitable especially for use with heavy ions.

The problem is solved in accordance with the present invention by a method having the features of claim 1. The dependent claims each define preferred and advantageous embodiments of the present invention.

According to the present invention, an ion beam therapy system is operated which comprises a grid scanner device, arranged in a beam guidance system, having vertical deflecting means and horizontal deflecting means for vertical and horizontal deflection of a treatment beam perpendicular to its beam direction so that the treatment beam is deflected by the grid scanner device to an isocentre of the irradiation site and scans a specific area surrounding the isocentre, irradiation being carried out on the basis of calculated radiation dose data. The accuracy of the calculation of the radiation dose data is verified by using a phantom, a discrepancy between the radiation dose calculated for the at least one measurement point of the phantom and the radiation dose measured for the at least one measurement point being determined and evaluated.

Different phantoms can be used for different media to be irradiated.

It is proposed, especially, that the calculated radiation dose values be checked for a plurality of measurement points in the phantom, it being concluded that the accuracy of the calculation of the radiation dose data is adequate if the average discrepancy, for all the measurement points, between the calculated and the measured radiation dose values does not exceed a predetermined first tolerance value and, for each individual measurement point, the discrepancy between the radiation dose calculated and measured for that measurement point does not exceed a predetermined second tolerance value, the first tolerance value being ±5% and the second tolerance value being ±7%.

In order to check that the geometric structures at the treatment site and planning parameters are correctly transferred from an image-forming device of the ion beam therapy system to the positioning means, a digital reconstruction, especially an X-ray reconstruction, of the phantom can be calculated, which is compared with an X-ray image taken of the phantom, in order to ascertain a possible discrepancy.

The present invention renders possible a clear improvement in the operational stability and operational safety of the ion beam therapy system and defines a checking plan having particular checking aspects that can be performed in the sense of an inspection test and/or a consistency test of the ion beam therapy system. This relates especially to the irradiation planning, in the course of which radiation dose data are calculated in the ion beam therapy system in dependence upon the patient being irradiated or treated.

The invention is described in the following by way of a preferred exemplary embodiment with reference to the accompanying drawings.

An ion beam therapy system, on which the present invention is based, is generally used in hospital buildings that are subdivided into a medical zone and an accelerator zone. A plurality of treatment or irradiation sites are provided for the treatment of patients. The supervisory control system of the ion beam therapy system comprises a plurality of supervisory control rooms, it being possible for technical supervisory control rooms to be provided for the individual treatment sites and for a main supervisory control room to be provided for the accelerator device. Laboratories for the dosimetry or for accelerator maintenance, or a PET device (positron emitter tomograph), can also be accommodated in the building. In addition, energy supply devices (especially for the accelerator device and the irradiation system) and cooling devices are provided. In order to ensure an adequate shielding action, the individual treatment rooms are bounded by thick walls and ceilings, which consist, for example, of concrete of a thickness of 2 m.

Since the basic structure of the ion beam therapy system is essentially not the theme of the present invention, only a brief description is given here.

Figure 1:
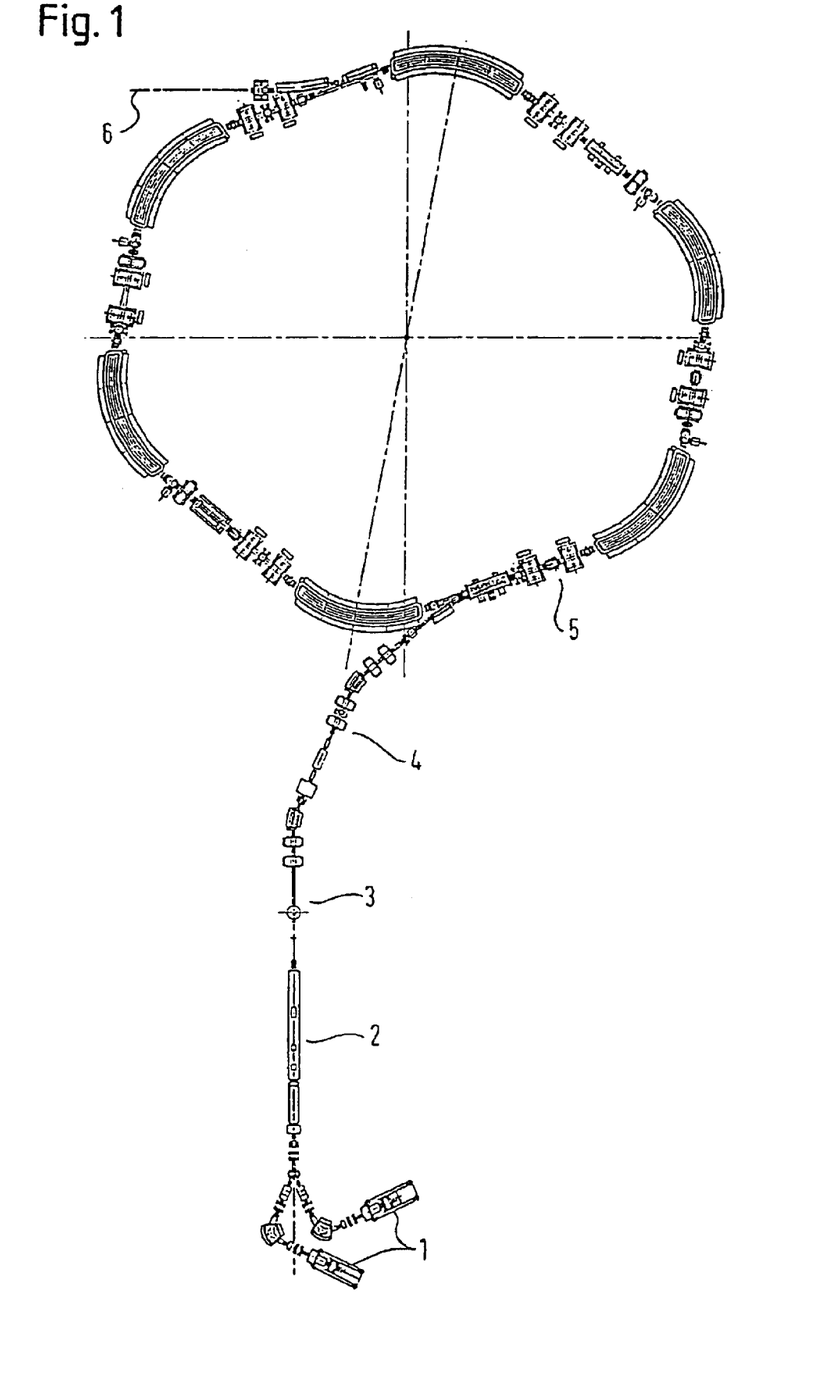
FIG. 1 is a simplified schematic representation of an acceleration device used in the present ion beam therapy system.

The ion beam therapy system comprises an injection system, which is shown in simplified form in FIG. 1 together with the accelerator device already mentioned hereinbefore.

The injection system comprises ion sources 1 of which the radiation is in each case fed, by way of low energy beam guidance channels with an arrangement of spectrometer magnets and quadrupoles, to a switching magnet that guides the radiation, inter alia by way of a further quadrupole arrangement and by way of a chopper arrangement provided for pulse formation, to a linear accelerator 2 (LINAC).

In the present exemplary embodiment there shall be used exclusively $^{12}C^{2+}$ ions, which are stripped to $^{12}C^{6+}$ in the beam guide between the linear accelerator 3 and the synchrotron ring 5. For that purpose, a stripper 3 is provided downstream of the linear accelerator 2. Owing to their physical and biological properties, those carbon ions have proved to be very effective in the treatment of tumours and have the advantages of a high physical selectivity and a high biological effectiveness and, in addition, offer the possibility of verification of the irradiation with the aid of a positron emitter tomograph (PET). By suitable selection of the carbon ions, the biological effectiveness can be controlled in such a manner that it is low in the plateau region of the Bragg curve and high in the region of the Bragg peak. Consequently, the target or the tumour can be treated with a comparatively high dose while the dose for the surrounding healthy tissue is minimised.

In order to ensure the use and acceleration exclusively of the type of ion intended, a charge spectrum of the beam present is recorded and evaluated in the high-charge injection system. By comparison of the recorded charge spectrum with a reference spectrum, undesired ions or irregularities can be detected and appropriate measures taken. This check can be carried out, for example, with each initialisation of an ion source 1.

The linear accelerator 2 is used for the initial acceleration of the ions fed to it, those ions then being delivered by an injection line 4 to the synchrotron 5. The injection line 4 comprises, in addition to the stripper 3 already mentioned, a further chopper arrangement for precise shaping of the injection pulses, dipole magnets for charge analysis, quadrupoles for adapting the radiation to the receiving capacity of the synchrotron 5 etc.

The injection system, which comprises inter alia the ion sources 1, the low energy beam guidance channels, the linear accelerator 2 (LINAC), the stripper 3 and the injection line 4, thus has the task of generating and analysing ion beams having desired particles, monitoring the contamination of the ion beams and controlling the ion beam intensity, accelerating the ions to a particular injection energy and determining the pulse length of the pulses injected into the synchrotron ring 5.

The synchrotron ring 5 serves for the final acceleration of the ions fed to it to a determined energy and comprises, for example, a plurality of deflection magnets, quadrupoles and sextupoles. In the exemplary embodiment shown in FIG. 1, there are provided, for example, six deflection magnets each having a deflection angle of 60°. Arranged inside the synchrotron 5 is a cooling means (not shown). By means of repeated injection cycles, the injected ions are accelerated from an energy in the region of a few MeV/u to an energy of, for example, more than 400 MeV/u. The treatment beam accelerated in that manner is extracted at a particular point in the synchrotron by way of a high energy beam guidance channel 6 and delivered to the individual treatment sites.

Although the horizontal and vertical broadening of the beam at the treatment site is generally variable, the demands for an "ideal" symmetrical and stable beam shape at the treatment site can be substantially taken care of by a suitable adjustment of the beam optics in the beam guidance channels.

The high energy beam guidance channel 6 comprises quadropole lenses, deflection magnets, beam analysis devices etc. In addition, a further chopper can be arranged downstream from the extraction point in the synchrotron 5, which in emergencies is used to interrupt the beam supply. In addition, a routine interruption of the extraction procedure, which serves to decouple the treatment beam from the synchrotron 5, can be provided after each grid scan section.

Figure 2:
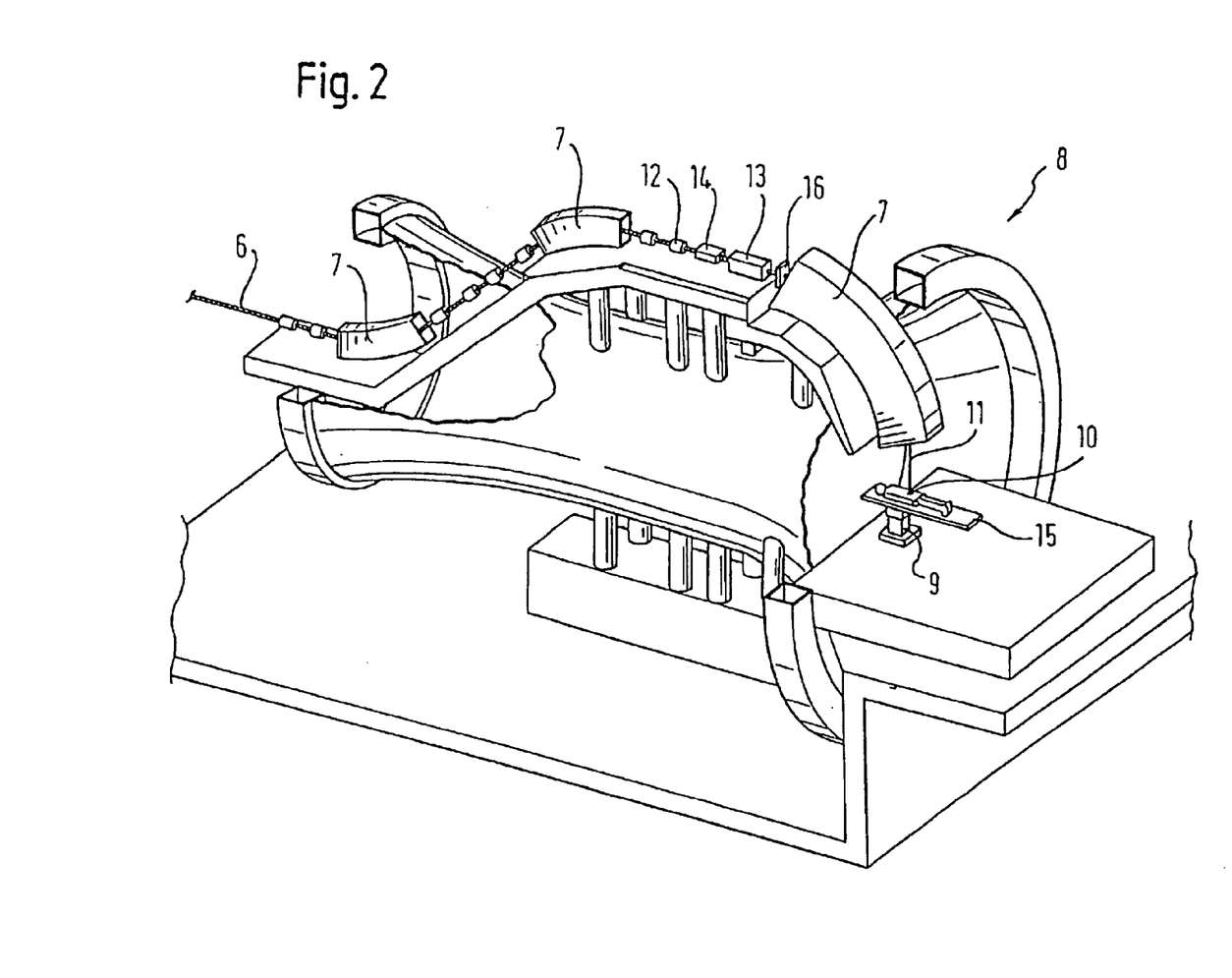
FIG. 2 is a view of a rotating cradle used in the present ion beam therapy system.

FIG. 2 is a perspective view of one of the rotating cradles 8, which are each provided at one of the treatment sites to which the treatment beam is delivered by way of the afore-described high energy beam guidance channel 6. The rotating cradle 8 rotates about a particular axis of rotation, while a patient to be treated lies on a patient couch 9 in locally fixed orientation and alignment. The region of the patient's body to be treated is in that arrangement located in the isocentre 10 of the treatment beam, the isocentre being defined as the point of intersection between the central beam 11 of the grid scanner described in detail hereinafter and an axis of rotation of the patient couch 9.

As can be seen from FIG. 2, the high energy beam guidance channel 6 is so constructed that the treatment beam, after entry into the rotating cradle 8, is deflected several times in one plane. There are provided for that purpose a plurality of quadrupole lenses 12 and dipole magnets 7, the first two dipole magnets 7 having identical deflection angles, for example 42°, and being arranged opposite each other, whilst the last dipole magnet 7 is a deflection magnet having a deflection angle of 90°, with the result that after the treatment beam 11 has entered into the rotating cradle 8 it is first deflected laterally out of the axis of rotation of the rotating cradle 8 and then guided parallel to the axis of rotation of the rotating cradle 8 in order subsequently to leave the last deflection magnet 7, via a beam outlet aperture, at an angle of 90° with respect to the patient couch 9.

In the exemplary embodiment shown in FIG. 2, the grid scanner arrangement provided in the present ion beam therapy system is arranged between the last quadrupole lens 12 and the last deflection magnet 7 of the rotating cradle 8 and comprises at least one horizontal grid scanner magnet 13 and at least one vertical grid scanner magnet 14. The grid scanner magnets 13 and 14 each deflect the ion beam 11 perpendicular to the beam axis 11 either horizontally or vertically, with the result that the ion beam 11 deflected in that manner, after leaving the last deflection magnet 7, scans a specific area surrounding the isocentre 10 in concurrence with a predetermined treatment plan. Owing to the arrangement of the grid scanner 13, 14 between the last quadrupole magnet 12 and the last deflection magnet 7, a high degree of flexibility can be achieved in the control, described in detail hereinafter, of the beam magnitude and the beam dispersion at the isocentre 10.

The grid scanner magnets 13, 14 are controlled by a control device (not shown) that is a component of the overall supervisory control system of the ion beam therapy system.

There are provided, in the region between the beam outlet aperture of the last deflection magnet 7 and the isocentre 10, monitoring means for monitoring the treatment beam 11. Those monitoring means, which are provided, for example, to ascertain and control the beam position, beam shape and particle flow, are explained in detail hereinafter.

As has already been mentioned hereinbefore, in addition a positron emitter tomograph (PET) can be provided for supervising the irradiation procedure, the image recorder (camera) of which is aligned in an in-beam position. The positron emitter tomography is preferably carried out during the treatment or irradiation. When a treatment beam impinges on tissue, positron-emitting isotopes are generated from the primary ions. Some of those isotopes, which differ from the primary ions solely as a result of the loss of one or two neutrons, stop almost in the same region as the corresponding primary ions. That stopping point of the so-called positron emitters can be determined for the purpose of monitoring the irradiation procedure by means of positron emitter tomography.

There has been developed for the above-described ion beam therapy system an extensive checking system, to be described in detail hereinbelow, for checking and controlling the important performance features of the therapy system.

A first section of this checking system is concerned with the generation of the treatment beam 11.

In addition to the checking, already described hereinbefore, of the type of ion, at the same time the radiation energy of the treatment beam is monitored. This is a requirement since it is necessary to adhere to the radiation energies required by the particular therapy. For that purpose, the monitoring means indicated in FIG. 2 comprise an absorber ionisation chamber system allocated to the isocentre 10 of the respective treatment site. The absorber ionisation chamber system measures the position of the Bragg peak at the treatment site for a few selected energy levels, which are activated during a therapy test cycle, the instantaneous radiation energy being derived from the measured position of the Bragg peak. In order to determine the position of the Bragg peak, the Bragg curves are measured in precise steps. If, on examination, there were to be a departure of the Bragg peak from the desired position of more than 0.5 mm, then intervention would be necessary. In order to examine consistency, the described checking procedure can be carried out prior to each block of irradiation procedures.

A further point of detail with regard to checking of the treatment beam concerns the monitoring of the level of intensity of the slowly extracted treatment beam at the irradiation or treatment site. The limited dynamics of the grid scanner puts an upper limit on the deflecting or scanning speed of the deflected treatment beam, the component that determines that limitation being the maximum current-increase speed of the magnet current supply devices. The scanning speed of the treatment beam depends on the particular intensity of the beam and the planned particle coverage. In order to ensure that the maximum scanning speed is not achieved during the irradiation, the particle rate extracted from the synchrotron 5 is not permitted substantially to exceed the desired value. If, on the other hand, the rate falls distinctly short of that value, the total irradiation time is extended, the supervisory control and surveillance or monitoring system in that case optionally being operated in the range of very small input currents, which can adversely affect the accuracy of the beam detection. Accordingly, in the present therapy system, measurement and protocolling of the particle intensities in the synchrotron is provided in the upper intensity range and measurement and protocolling of the particle rate delivered to the irradiation site is provided for all levels of intensity for a plurality of energies over a few minutes. The particle rate fed from the accelerator to the irradiation site is between $2 \times 10^6$ and $2 \times 10^8$ ions per extraction from the synchrotron 5. The departure of the particle rate from the predetermined desired value may be a maximum of 30% above and a maximum of 50% below that value. If those limit values are transgressed, an appropriate intervention is necessary. In order to check the consistency of the therapy system, such an inspection may, for example, be carried out daily.

The same dependencies of energy variation, intensity variation and focusing variation must be taken as a basis for data supply for the accelerator, for irradiation planning and for grid scan programming. In order to ensure that that is the case, the data inputs generated accelerator-wise after the last therapy programming should be compared with those used for the grid scan programming and irradiation planning. Departure from those data inputs is not permissible. In order to check consistency, such a check should be carried out prior to each block of irradiation procedures.

During irradiation, the sections of the accelerator that are necessary for the therapy are blocked against (external) intervention in order to avoid intentional and unintentional false settings. At the same time, operational states are activated for all components and desired value data for the apparatus filed in the memories, e.g. EPROMS, exclusively, are accessed. The function of blocking the accelerator against intervention can be checked by setting up a "super cycle" that contains both test and therapy accelerators. Monitoring means or detectors, such as, for example, (described in detail hereinafter) profile grids, luminous targets and ionisation chambers, are moved into the high energy beam guide 6 to the rotating cradle 8, and beam-influencing elements of the high energy beam guidance channel 6 and of the synchrotron 5 for the therapy accelerator are deactivated. Blocking of the accelerator is then activated and all test accelerators are deactivated, while the therapy accelerator is activated. In addition, all previously deactivated components are activated for the therapy accelerator, and the inserted profile grids, luminous targets and ionisation chambers are moved out again. Subsequently, switch-off commands are sent to individual magnets and adjustment commands are sent to beam guidance diagnosis components, those commands normally not being allowed to have any effect owing to the blocking of the accelerator. There is otherwise an error, which must be corrected accordingly. This check can be carried out prior to each block of irradiation procedures in order to check consistency.

It must be possible, for safety reasons, for the extraction of the treatment beam from the synchrotron 5 to be terminated within less than 1 ms after an appropriate signal from an interlock unit of the therapy system. This is effected by a special quadrupole in the synchrotron rapidly being switched off. The time between a request by the supervisory control and safety system for the beam to be terminated and the absence of the beam at the irradiation site is of crucial importance both for the grid scanning operation when there is a change between successive isoenergy levels, those levels corresponding to areas to be irradiated with constant energy, and for a possible emergency shutdown of the system in case of error. There is accordingly provided a test that measures the total time, that is to say both the reaction time of the request and the reaction time of the beam termination. To that end, the supervisory control system generates an appropriate signal which simulates the ending of an isoenergy level, or an interlock condition, that is to say a condition for an emergency shutdown, is generated. The particle count after a termination is then measured by the supervisory control system, wherein 1 ms after termination the count is not permitted to be greater than $10^4$ particles/s. In addition, using a storage oscillograph and a pulser, which are installed in fixed position in the technical supervisory control room of the therapy system, a measurement is carried out that evaluates the output signal of the current/voltage converter of one of the ionisation chambers in order to check the afore-described measurement of the supervisory control system. In that second measurement, too, it should not be possible for any beam to be detected 1 ms after termination. The following time checks during a termination should be made one after another: the beginning of the extraction time, the middle of the extraction time, the end of the extraction time and beyond the extraction time. The check should be carried out daily as a consistency check.

At the end of each irradiation procedure it is necessary, in respect of the accelerator, for a protocol to be drawn up that documents both the settings of important accelerator components during the irradiation procedure and selected beam diagnosis measurement results. In order to test the functionality of the protocolling and the protocol contents, it is proposed that a reference therapy cycle be activated and that the protocol program be called up. The protocol data drawn up by the protocol program can then be compared with the expected data, intervention being necessary when the protocol is incomplete or when a protocolled apparatus error exists. In order to check consistency, this checking procedure can be carried out prior to each block of irradiation procedures.

A second section of the checking system is concerned with checking the guidance of the treatment beam (upstream of the irradiation site).

Starting from the accelerator, it must be ensured that termination of extraction is effected when there is a termination request. Should the treatment beam not be terminated by the termination request, that fact is ascertained by the supervisory control system and safety system by means of an intensity measurement, and termination of the beam is requested again by way of a separately provided redundant channel. That second request acts on a corresponding deflection dipole of the high energy beam guidance channel 6. In order to check the functionality of that redundant termination of extraction, the alarm line provided for the first termination of extraction is artificially interrupted. In that case, the afore-described second termination of extraction ought to be triggered automatically, which can be tested analogously to the above-described test for the normal termination of extraction. If termination of extraction does not occur within 10 ms, appropriate intervention is necessary. In order to check consistency, that test can be carried out prior to each block of irradiation procedures.

The operation of connection and disconnection of the dipoles arranged in the high energy beam guidance channel 6 can be tested by means of a further test. For reasons of patient safety, disconnection of the last two deflection magnets in the high energy beam guidance channel 6 prior to irradiation (after blocking of the accelerator) is activatable only from the technical supervisory control room by way of special cable connections to the power supply unit for those magnets. As a result of such a disconnection, the beam supply to the irradiation site is stopped. Connection of those magnets can be carried out only from the technical supervisory control room by way of a special signal and cannot (as usual) be carried out from the main supervisory control room of the accelerator. The operation of this connection and disconnection is tested, the corresponding connections/terminals also being tested at the same time. In order to check consistency, this test is carried out prior to each block of irradiation procedures.

A third section of the checking system is concerned with checking the beam guidance at the irradiation site.

In accordance with a first aspect of that checking section, the zero position of the treatment beam is monitored. In order to ensure accurate positioning of the beam at the isocentre 10 following deflection of the beam 11 by the grid scanner magnets 13, 14, the axial position of the treatment beam 11 in the last portion of the beam guide to the irradiation site must be checked for the entire energy and focusing range. For that purpose, profile grids 16 are moved into the beam path downstream of the grid scanner magnets 13 and 14 and at the beam outlet window, and test cycles are generated over the entire energy and focusing range, in the course of which the profile grids are evaluated individually and the beam parameters ascertained in the procedure are protocolled. When the profile grid arranged at the beam outlet window is measured, the profile grid 16 arranged upstream thereof must be moved out. By evaluating the beam parameters delivered by the profile grids it is possible to determine the beam position and the beam angle both in the horizontal and in the vertical direction. From the beam positions of the profile grids, the position of the treatment beam to be expected at the isocentre 10 is determined and then the protocol is checked. If a position error of ±25% with respect to the required beam half-value width is determined for the isocentre 10, appropriate intervention must be carried out. In order to check consistency, this test can be carried out daily.

According to a further aspect of that checking section, the absolute beam location and the location stability of the treatment beam at the irradiation site are checked. Adherence to the absolute beam position is a prerequisite for the implementation of the treatment or irradiation plans. The absolute location must therefore be measured using location-sensitive detectors of the supervisory control system. The relative location stability of the treatment beam in the isocentre of the irradiation site determines the accuracy with which an irradiation plan can be carried out. The location of the treatment beam is measured and checked online, that is to say continuously, during an irradiation procedure. If there are departures from the desired location inside a tolerance limit predetermined by the irradiation plan, the irradiation is discontinued or an appropriate intervention is activated. Each location-sensitive detector is checked separately.

The check is carried out using a profile grid and location-sensitive detectors, such as, for example, multi-wire chambers.

When profile grids are used, the absolute beam position in the isocentre 10 is checked by means of a luminous target or a film at the site of the isocentre. In that checking procedure, the position of the profile grid is adjusted with the isocentre made visible on the luminous target or film by a laser cross. By means of the grid scanner magnets 13, 14, the treatment beam 11 is statically deflected into the isocentre 10 and the location coordinates obtained by the profile grid measurement are compared with the predetermined desired values. This can be carried out, for example, at regular intervals, for example at approximately every tenth energy level.

When multi-wire chambers are used for the online examination and control of the beam position, two multi-wire chambers are positioned at a distance of approximately 970 mm and 790 mm upstream of the isocentre 10 and so aligned by means of a laser beam that the central beam extending through the isocentre 10 runs perpendicularly through the centre of the multi-wire chambers. By means of the grid scanner magnets 13, 14, the beam is statically deflected, for example at five different energies, into each of five different positions within the irradiation area (that is, above and below in each case to the left and right, and also in the centre). The location of the setting is measured by the supervisory control system and compared with the desired values.

Since the multi-wire chambers are located at different distances upstream of the isocentre, the projection of the irradiation field in the two multi-wire chambers is reduced by different factors. By applying the rules of beam geometry and radiation law, the following reduction factors are obtained:

Multi-wire chamber 970 mm upstream of the isocentre:
X coordinate: reduction factor 0.890
Y coordinate: reduction factor 0.876
Multi-wire chamber 790 mm upstream of the isocentre:
X coordinate: reduction factor 0.910
Y coordinate: reduction factor 0.899

Prior to the absolute beam position being checked by the multi-wire chambers, a calibration of their absolute positions should be carried out. For that purpose, after alignment of and fixing of the position of the multi-wire chambers, a film positioned absolutely by means of the above-mentioned laser cross is irradiated at five positions. The zero point of the beam determined by way of the film is compared with that calculated from the multi-wire chambers. The difference or discrepancy then gives correction offset values for calculating the location. Those correction offset values are taken into consideration in the desired position values, the absolute position of all five points being compared with one another.

Using the multi-wire chambers calibrated in that manner, the absolute beam position is then checked, control being so carried out that the difference in position determined in that manner corresponds to a maximum of 25% of the half-value width of the beam profile. This intervention threshold relative to the half-value width of the beam profile has proved practicable since all geometric parameters of an irradiation plan scale with the half-value width and, in particular, the quality of the generated particle coverages necessary for patient operation is achieved. For carrying out a consistency check, only the afore-described multi-wire chamber measurements should be used, since the installation of an additional profile grid in the isocentre would be very expensive for daily operation.

A further aspect of that checking section comprises the monitoring and control of the absolute beam profile width and of stability over time. It is necessary to adhere to the beam focusing delivered by the accelerator device according to the request by a pulse central control of the supervisory control system, since the treatment or irradiation plans are based on those values. To that end, the absolute beam profile width in the isocentre 10 is checked with the aid of a profile grid, the position of the profile grid being adjusted with the isocentre made visible by a laser cross on a luminous target or on a film. The treatment beam is statically deflected by the grid scanner magnets 13, 14 into the isocentre, it being possible for that to be carried out, for example, at approximately every tenth energy level. The beam widths obtained by the profile grid measurement are compared with predetermined desired values, control being carried out in such a manner that a maximum departure of the beam width from the predetermined desired value of ±50% is observed. This applies especially to the energy range above 200 MeV/u.

Checking the consistency of the ion beam therapy system can on the other hand be carried out using the multi-wire chambers, already described hereinbefore, which are located, respectively, at a distance of 970 mm and 790 mm upstream of the isocentre 10. Before the actual checking operation, calibration of the absolute width measurement of the two multi-wire chambers is carried out. In that procedure, a film is irradiated with horizontal and vertical stripes, each beam being generated by an extraction from the synchrotron with fixed focusing. In that manner it is possible, depending on the selectable focusings, for example for seven beams to be generated. The beam widths determined by way of the irradiated film are compared with those measured by the multi-wire chambers (location chambers) in order to obtain correction offset values therefrom that can then be taken into consideration again in the desired values. Then, by means of the thus calibrated multi-wire chambers in conjunction with the supervisory control system, the half-value width of the beam profile and its consistency or stability over time is measured and monitored, this being carried out especially at different energies and intensities for each of the selectable focusings.

The above-described increase of the intervention threshold from 20% to 50% of the half-value width in the measurement of the absolute beam profile width compared with the measurement of the absolute beam location is compatible with the requirement for homogeneity, since the spacing of the beam positions in the context of the irradiation plan is set at 33% of the half-value width.

A few elements for analysis and modulation of the treatment beam are usually located upstream of the isocentre, such as, for example, the beam outlet window, detectors or a ripple filter. Those elements bring about a scattering of the treatment beam, which increases markedly as the beam energy decreases. As a consequence, for physical reasons it is not possible, or possible only with difficulty, to adhere to the originally requested beam width in the lower energy range (energies <200 MeV/u). The result in that case would be that the upper tolerance values would be exceeded, and so that effect needs to be taken into consideration in irradiation planning.

Figure 3A:
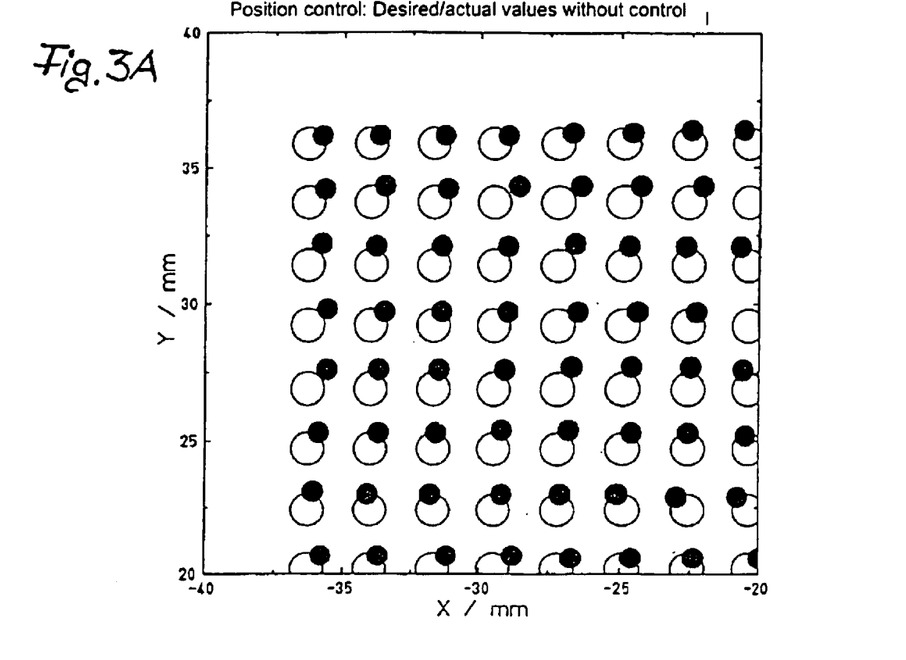
FIGS. 3A and 3B and FIGS. 4A and 4B are, in each case, diagrams that illustrate the advantageous effects of beam position control measures in the ion beam therapy system shown in FIGS. 1 and 2.
Figure 3B:
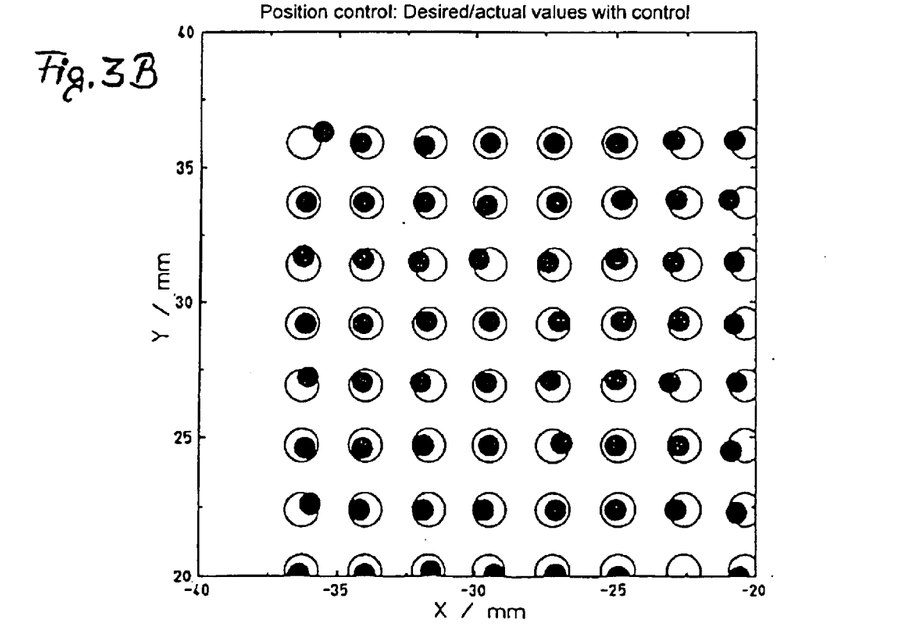
Figure 4A:
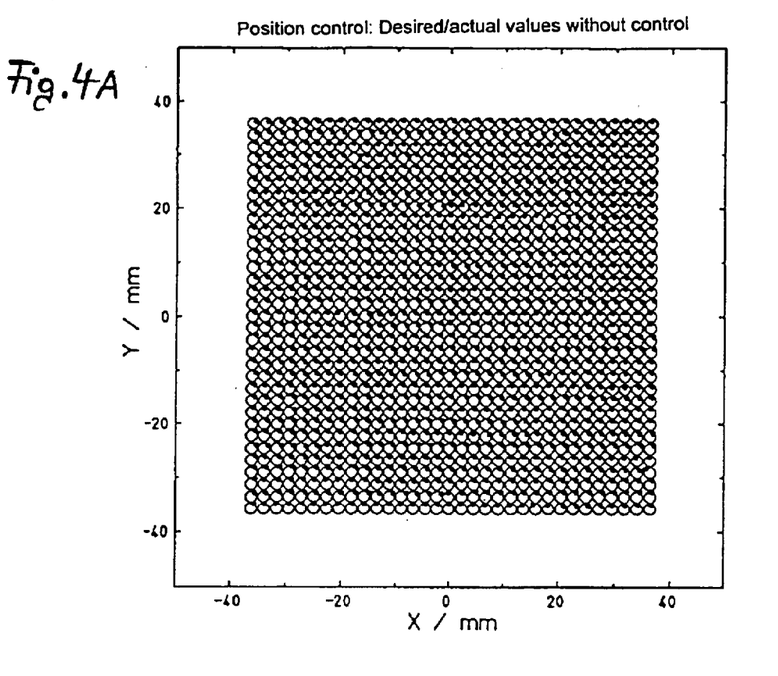
Figure 4B:
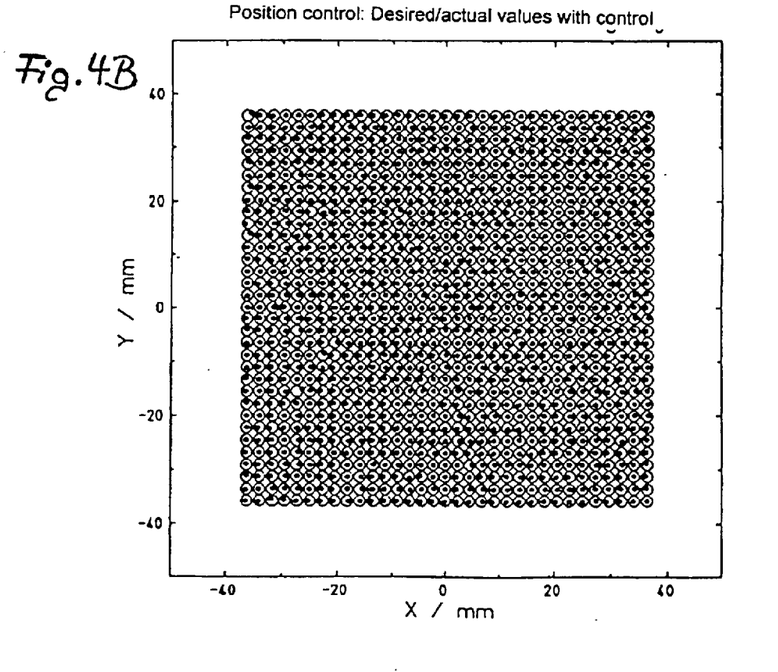

The effects of the above-described monitoring and control measures with respect to the beam zero position, the absolute beam location, the absolute beam profile width and the stability thereof over time can be seen in FIGS. 3A/B and FIGS. 4A/B. FIGS. 3A and 3B correspond to an enlarged view of the diagrams shown in FIGS. 4A and 4B, respectively, FIGS. 3A/4A showing beam positions without the position control proposed hereinbefore and FIGS. 3B/4B showing beam position with the position control. It can be seen from the diagrams that, as a result of using the position control etc., a considerably more stable beam position can be achieved, whereas without position control there are some marked departures from the desired beam position.

A further aspect of this checking section is concerned with monitoring the particle count in the treatment beam, that is to say, monitoring the variation in the particle count. So as to prevent the measurement range for particle count measurements from becoming too large, the intensity of the treatment beam delivered by the accelerator should vary only within certain tolerance limits. It is proposed in the present case that the intensity of the treatment beam be measured using the ionisation chambers in conjunction with the measurement apparatus of the supervisory control system, and that the particle count be averaged over a time window of 300 $\mu$s. The particle counts then measured are permitted within the time window to correspond to a maximum of five times the value of the previously ascertained average value in order not to trigger an intervention. As a result of taking those steps, a more reliable measurement range can be selected with which even particle counts that are, for example, higher by a factor of 10 than the previously calculated average value can still be measured correctly. Should even higher particle counts arise, an alarm is triggered and the interlock unit, already mentioned, triggers switching off of the beam. Care must be taken, however, that this checking aspect relates only to the presetting of the detectors, and has no direct influence on the energy dose or the like. Even in the event of a variation in the particle count lying appreciably above the previously defined intervention threshold, the homogeneity of the particle coverages, described hereinafter, may be sufficient as a decisive quality criterion.

Finally, with regard to a reliable and stable beam guidance at the irradiation site, the desired positions of all movable components between the last deflection magnets of the high energy beam guidance channel 6 and the rotating cradle 5 should be checked regularly, since any object located in the beam guide has an adverse effect on the beam quality at the irradiation site. It must therefore be ensured that no movable components of the beam guide are to be found in the beam path. To that end, there are connected to the corresponding movable components limit switches of which the states can be automatically and individually checked by the supervisory control system. In order to check consistency, this should be repeated prior to each block of irradiation procedures.

A fourth section of the checking system is concerned with checking features that are associated with the irradiation control unit of the ion beam therapy system.

The electric charge generated in the afore-described ionisation chambers of the supervising or monitoring system of the therapy system, which charge serves to determine the particle count, depends on the pressure and the temperature of the ionisation chamber gas, so that both those variables have to be monitored and protocolled during irradiation. The pressure and the temperature of the gas of the ionisation chambers are measured by means of electrical sensors, the measurement values being ascertained approximately once per minute by the supervisory control system and converted with entered calibration factors into absolute units (hPa and ° C.) and displayed digitally. The trend of the measurement values over time can be illustrated graphically in a trend diagram. The sensors are calibrated by means of reference measurement devices. The calibration of the sensors installed in the ionisation chambers should be repeated prior to each block of therapy irradiation procedures. In addition, the atmospheric pressure and the room temperature at the site of the monitoring system are measured by absolutely calibrated devices and ascertained by the supervisory control system and also protocolled in each irradiation procedure. Consequently, for the (daily) checking of the ionisation chambers, the absolute values for atmospheric pressure and room temperature can be read off directly at the reference measurement devices, compared with the values displayed by the supervisory control system and protocolled. The measurement values registered in the daily calibration of the monitoring system serve as reference values in that procedure. If there is a discrepancy of 20 hPa or 5° C., an alarm is triggered by the supervisory control system.

In addition, the loading of programs and data sets into the control computers of the ion beam therapy system must be checked. This is necessary in order to be able correctly to load data required for the irradiation of a patient into the sequence control of the system. Only if all data are correct may irradiation of a patient be commenced. For that purpose, using special programs in the server computers of the supervisory control system, programs and data are written into the individual processors of the control computers, read back and compared with the programs and data stored in the individual memories, such checking programs being performed automatically prior to each irradiation procedure. Only when the reloaded data correspond precisely to the data stored in the data memories of the supervisory control system is it possible to start from a state of being safely under control. When discrepancies exist, an alarm signal is generated and the afore-described interlock unit, which serves to prevent an irradiation procedure, cannot be released.

A further checking aspect is concerned with the connection of the currents for the deflection magnets 13, 14 of the grid scanner. Care must be taken that the current values of those deflection magnets achieve a specific desired value set in the magnet supply devices, both in terms of value and time, within specific tolerance limits. For that purpose, the time between setting a magnet current value in the magnet supply devices and reaching the appropriate stable magnet current is measured for different current values. The maximum current accuracy that can be tolerated in respect of a departure from the set magnet current value is 0.3 A. The maximum adjustment time that can be tolerated when there is a current change of 2 A is 175 $\mu$s in the x direction and 325 $\mu$s in the y direction. When those tolerances are not adhered to, the irradiation must be terminated. In order to check consistency, this test can be carried out prior to each block of irradiation procedures.

Finally, it must also be ensured that the number of irradiation points active when a termination condition arises is stored permanently, that is to say, safeguarded against loss of power. This renders possible continuation at a later point in time of the irradiation approved by authorised personnel. The functionality of this implemented safety function can be checked by loading a particular irradiation or treatment plan into the supervisory control system and carrying out the plan without irradiation, that is to say simulating it. At a particular irradiation site, the voltage supply of the sequence control is switched off and, after restarting the system, the last irradiation site is read out and compared with the irradiation site when the voltage supply was switched off. If the two readings do not agree, appropriate intervention is carried out. To check consistency, this inspection is carried out prior to each block of irradiation procedures.

A fifth section of the checking system is concerned with checking the functionality of the interlock unit, already described hereinbefore, of the ion beam therapy system.

Accordingly, for example all apparatus parameters relevant from a safety standpoint for triggering an emergency shutdown of the system when an interlock event or interlock condition exists must be checked. Shutdown of the treatment beam 11 can be carried out only when an interlock event is detected. Therefore all sources that can lead to an interlock event must be individually simulated in a test and the triggering of the interlock, that is to say the generation by the interlock unit of signals that result in the emergency shutdown of the treatment beam 11, must be checked. During operation, the interlock unit monitors, for example, the signals of the above-described limit switches of the movable components in the beam guide, the states of the magnet supply devices of the grid scanner magnets 13 and 14, the ionisation chambers in respect of the voltage supply, a data overflow of the data transfer, the adherence to the intensity limit values and the synchronization of the individual ionisation chambers, the electronics of the beam position measurement device and the beam position itself, the high voltage and the gas flow of the individual detectors, a possible interlock by the sequence control computer, the position of the patient couch, a possible interruption of the immobilisation of the patient (for example when the mask at the irradiation site is opened or when the patient moves), the readiness for operation of all computer programs and a possible emergency shutdown or release of an irradiation procedure by the medical operating console of the therapy system etc., If triggering of the interlock does not occur when an interlock condition exists, intervention in the therapy system and elimination of the errors is necessary. To check consistency, this inspection should be carried out daily.

The functionality of the manual emergency shutdown by way of the medical operating console must likewise be checked, since manual emergency shutdown must be guaranteed at all times.

Finally, it is necessary to check on the individual consoles of the ion beam therapy system, especially of the technical supervisory control rooms and of the main supervisory control room, the displays of all of the conditions that are relevant in terms of safety. The display of those safety-relevant conditions serves for the rapid detection and elimination of errors and gives the operating personnel information concerning the current state of the irradiation procedure. Those displays of the alarm conditions can be checked together with the above-described test of the interlock unit. In order to check consistency, this test should be carried out prior to each block of irradiation procedures and after each change of the supervisory control system or of the programs.

A sixth section of the checking system is concerned with checking of the medical devices for the patient positioning of the ion beam therapy system.

Thus, for example, the accuracy of the stereotactic determination of coordinates of a target point should be checked by means of a CT or MR procedure, since the accuracy of the stereotactic image formation is a crucial factor for the overall accuracy of the irradiation. For that purpose, it is possible for any desired target point to be represented inside a spherical phantom by means of a special specimen body, the centre point of which can be visibly represented by means of the image-forming method. The spherical phantom is inserted into the stereotactic frame so that the centre point becomes an unknown target point. The stereotactic coordinates are then ascertained one after the other in terms of time using the applied X-ray, CT or MR method, wherein in the tomographic method the layer spacing should be 1 mm. Since the X-ray method is accurate to $\frac{1}{10}$ mm, the accuracy of the determination of the target point by CT and MR can be ascertained by comparison with the X-ray method, that is to say, the radial spacing between the position of the target point determined by X-ray image and the position determined by the CT or MR method is checked. The radial spacing should not exceed 1.5 mm. For the purpose of checking consistency, it is sufficient for this test to be carried out annually.

As a further checking aspect it is proposed that the accuracy of the position of the isocentre between the axis of rotation of the patient couch 9 and the central beam 11 of the grid scanner 13, 14 be checked since the isocentre, defined as the point of intersection between the axis of rotation of the patient couch 9 and the central beam 11 of the grid scanner 13, 14, is the connecting element in the positioning between planning and irradiation. A check for consistency should be carried out prior to each block of irradiation procedures.

In order to check the isocentre in relation to the axis of rotation of the patient couch 9, a metallic specimen body (2–3 mm in diameter) is introduced, with the aid of lasers, into the nominal isocentre, that is to say into the nominal axis of rotation of the patient couch 9. The specimen body is maintained in fixed position by means of a plumb bob, which is centred precisely on the centre point above the specimen body. On rotation of the patient couch 9 about the axis of rotation, the extent to which the specimen body moves in relation to the plumb bob is ascertained. This procedure is carried out at at least three different levels of the patient couch 9, with a maximum displaceability of the patient couch 9 up or down of 15 cm, for example at the level of the isocentre 10 and with a minimum of 15 cm distance above and below. The maximum departure allowable is 1.0 mm in the direction of the beam and only 0.5 mm perpendicular to the direction of the beam. Variations that are in the beam direction are less critical, since dose distributions in the patient are not affected by such variations.

In order to check the isocentre in relation to the central beam 11, the position of the isocentre is, by definition, fixed on the axis of rotation of the patient couch 9 below the plane for the straight-ahead beam, and is ascertained relative to wall markers by means of an optical measurement system. Checking the position of the specimen body relative to the central beam 11 is carried out by a film measurement, a verification film being irradiated, downstream of the specimen body viewed in the direction of the beam, with a (undeflected) central beam, the half-value width of which is greater than the diameter of the specimen body, with the result that the position of the specimen body is projected on the verification film relative to the central beam. In this case the intervention threshold is at a maximum 25% departure from the half-value width of the primary beam.

In addition, the accuracy of the laser alignment on the isocentre 10 must be checked, since the lasers mark out the isocentre 10. In this procedure, following positioning of the specimen body in the isocentre 10, the lasers are aligned onto the centre point of the specimen body by means of optical measurement, and the departure of the laser lines from the horizontal and vertical are checked, the maximum departure allowed in each case being 1 mm. In order to check consistency, the image of the lasers on the opposite-lying walls or on the floor is marked out and then used as a reference value.

A further checking aspect is concerned with the accuracy of the alignment of the X-ray tubes and of the target cross on the opposite-lying recording stations, since the X-ray method represents an additional procedure for marking out the isocentre 10. After positioning the specimen body in the isocentre 10 by means of optical measurement, that is to say using lasers, X-ray images are taken in the three spatial directions and the spacing between the projected image of the specimen body and the target cross on the X-ray image is ascertained. The image of the specimen body should be projected precisely onto the image of the target cross, so that the maximum permissible spacing between the projected image of the specimen body and the target cross is 1 mm.

Owing to the isocentric irradiation of the patients, it is also necessary for the accuracy of the display of the angular scale of the isocentric rotation of the patient couch 9 to be checked, and this can be carried out analogously to the provisions of DIN 6847-5, point 12.2.4. The maximum tolerable inaccuracy is 1°.

The spatial stability of the isocentric rotation of the patient couch 9 should likewise be checked, since a corresponding stability is a prerequisite of the definition of the isocentre 10. This check can be carried out analogously to DIN 6847-5, point 14.2, the intervention threshold being an inaccuracy of 1 mm.

It is finally also proposed that the accuracy of the placing and positioning of the patient is checked, since accurate patient positioning is a prerequisite for proper irradiation for the tumour in question. In that connection, for the inspection test and to check consistency (prior to each block of irradiation procedures) of the therapy system, the unknown stereotactic coordinates of the centre point of a specimen body, which has been fixed within the stereotactic base ring, are ascertained as the target point and, with the aid of the stereotactic targeting device and by means of transverse movement of the patient couch 9, the centre point is brought into the isocentre 10. In that position, X-ray images are taken in the three spatial directions and the spacing of the position of the specimen body from the target cross is determined on the three images. The maximum radial spacing allowed between the centre point of the specimen body and the isocentre is 1.5 mm. Otherwise an appropriate correction of the placing of the patient is necessary.

A seventh aspect of the checking system is concerned with irradiation planning, in the course-of which especially the radiation dose values intended for a particular irradiation procedure are calculated.

First of all it must be ensured that it is always the same ground data sets that are used for planning irradiation procedures, that is to say for calculating each radiation dose. This can be effected by comparing the name, the date and the size of the data files containing the ground data with the correct designations of a previously taken backup copy. This happens automatically each time the dose calculation algorithm is called up.

Also, the identity of the values of the actual ground data sets with the corresponding values of a backup copy must be checked in order to ensure that the ground data sets have not been changed in an uncontrolled manner. Also carried out here is a comparison of the contents of the actual ground data sets with the backup copy by means of a computer program, which program should be initiated especially prior to each block of irradiation procedures.

According to DIN 6873 part 5, irradiation planning systems, it is necessary in addition for the reference values in the ground data set to be checked once a month. This point of detail can be omitted in the present irradiation planning with heavy ions since the depth dose distributions, that is to say the energy loss data as a function of the depth, are stored as absolute values relative to the input fluence. No special reference value for the dose is therefore recorded. The ground data sets used are already checked in the manner described above.

An important aspect in checking the irradiation planning is checking the accuracy of the dose calculation (carried out automatically in the ion beam therapy system) for a planned irradiation procedure as a function of the ground data present and the dose calculation algorithms used, it being necessary to distinguish between the irradiation of a homogeneous and a non-homogenous medium. In both cases checking the dose calculation can be carried out by using a phantom, and this procedure is described in detail below.

In order to check the calculated dose for a homogeneous medium in the irradiation planning program of the ion beam therapy system, a plurality of measurement points, for example 10 measurement points, are defined in the calculated dose distributions or CT sections, at which measurement points the calculated physical dose is to be verified experimentally. The verification is carried out in a water phantom, ionisation chambers being positioned in the water phantom at the coordinates corresponding to the desired measurement points. The irradiation planning program calculates for the individual measurement points, in addition to the energy dose values related to water, also the coordinates thereof in the phantom used. The phantom is then irradiated using the control parameters calculated by the irradiation planning program, the values ascertained by the ionisation chambers being converted into energy dose values in order to verify the calculated dose values.

The verification is carried out for a plurality of irradiation plans, preference being given to the verification of six typical irradiation plans of which three are concerned with hypothetical target volumes in the water phantom and three are concerned with the irradiation of patients. The latter irradiation plans are thereafter used as standard patient plans. The values calculated by the irradiation calculation program serve as reference values for the consistency check that is to be carried out.

The intervention threshold laid down is that the maximum permitted discrepancy between the calculated and the measured radiation dose values is in total, that is to say on average, ±5% of the dose of the target irradiation volume. It is in addition laid down that the maximum permitted discrepancy for an individual measurement point is ±7%.

The above-described procedure relates especially to the inspection test of the ion beam therapy system. In order to check consistency, it is sufficient to verify only two in each case of the above-described standard plans to check the consistency of the calculated dose distributions, and to compare those with the dose distributions to be determined experimentally. The consistency check should be carried out prior to each block of irradiation procedures.

In order to check the accuracy of the dose calculations as a function of the ground data, of the irradiation calculation algorithms used and of the approximation for a non-homogeneous medium used, a spherical solid-body phantom can be employed that consists of a material equivalent to water and is constructed from individual layers into which various non-homogeneities can be inserted in order to simulate different non-homogeneous bodies. Those non-homogeneities are disks, which consist of various tissue-equivalent materials (for example corresponding to the material of the lungs, of a soft or hard bone, of soft parts or of bound water) or simply air (when a disk is not inserted). In that case, too, up to 10 measurement points are defined in the phantom for the verification, at each of which the radiation dose is both calculated by the irradiation planning program and ascertained using a group of simultaneously measuring ionisation chambers and compared therewith.

It is proposed, for the inspection test, that three different phantom structures be made for investigating the calculated dose distribution behind boundary layers of different materials (for example air/water and bone/water), in thin non-homogeneities and in thick non-homogeneities.

The proposed tolerance threshold in the investigation of the calculated dose values for non-homogeneous media is a maximum permitted average discrepancy between the calculated dose values and the measured dose values of all measurement points of ±5% and a maximum permitted discrepancy for an individual measurement point of ±7%. In order to check consistency, the above-described tests can be carried out prior to each block of irradiation procedures.

The dose calculations can also be verified by using an irregularly shaped test phantom. In that case use is made of a test phantom that consists of water-equivalent material and, for example, is modelled on a human head. As described hereinbefore, up to 10 measurement points are defined in the phantom for the verification. Furthermore, irradiation parameters are laid down for a suitable target irradiation volume in the head phantom and the test phantom is aligned with the aid of the stereotactic base ring. The energy dose values related to water calculated by the irradiation planning program of the ion therapy system at the selected measurement points are then compared with reference to the values measured at those measurement points with the ionisation chambers, and again the maximum permitted discrepancy for all measurement points is ±5% of the dose of the target irradiation volume, whereas the maximum permitted discrepancy for each individual measurement point is ±7%. In order to check consistency, this test can be carried out prior to each block of irradiation procedures.

A further aspect in checking the irradiation planning concerns the inspection of the image-forming process used in the ion beam therapy system so as to ensure a correct transfer of the geometric structures (for example of the target irradiation volume and of the contours of the patient) and of the planning parameters from the image formation to the positioning. For that purpose, as in the verification of the calculated radiation dose values in non-homogeneous medium, a phantom having disk-shaped or ring-shaped inserts can be used, it being possible for the non-homogeneous inserts in this case in addition to have different diameters. An image of the phantom is taken, and from the CT data so obtained digital X-ray reconstructions are calculated for the three main directions in the rotating cradle 8 (see FIG. 2). A verification of the planning geometry is then carried out in the three main directions with the aid of X-ray images of the X-ray positioning system. That procedure can be carried out at different angles of the patient couch 9 shown in FIG. 2, for example at 0°, 45° and 90°. In that manner the shape and the position of the non-homogeneities in the digital X-ray reconstruction relative to the X-ray images of the X-ray positioning system are verified. The tolerance thresholds laid down in this case are that both the maximum permitted positional discrepancy and the maximum permitted discrepancy in respect of the shape of the rings of the phantom is 2 mm. The consistency check can again be carried out prior to each block of irradiation procedures.

In order to increase operational safety, it is in addition necessary to monitor the maintenance and further development of the irradiation planning programs used in the ion beam therapy system. It is possible, following a further development of the irradiation planning programs, that an incorrect version of the program may be used in error. In order to avoid that and to ensure that the correct versions of the various modules are always used, the supervisory control system of the ion beam therapy system is so constructed that, each time an irradiation planning program is called up, version numbers with the date of the respective program are displayed which are to be compared by the user with data in a protocol book.

It must likewise be ensured, in the event of a further development of the irradiation planning program, that is to say when a new version exists, that that version becomes effective only after a renewed inspection test. This can be effected by complete dose distributions being calculated as described hereinbefore for a homogeneous medium, a non-homogeneous medium and for an irregularly shaped phantom, and being stored as a backup copy. When the new program version is used, those stored dose values can be used as reference values for verification of the functionality of the new program version, since it will also be necessary when the new program version is used for the same dose values to be calculated for the same phantom. This check should therefore be carried out after any change to the irradiation planning program.

An eighth section of the checking system is concerned with the inspection of the grid scanning procedure and the dosimetry.

A first checking aspect of this checking section is concerned with the particle count monitoring or supervising means of the ion beam therapy system, which in the case of the present exemplary embodiment—as has already been described—consist of large-area ionisation chambers.

In that connection, for example the consistency of the calibration factors of those ionisation chambers must be checked, since the calibration factors are permitted to vary only within the bounds of variations in atmospheric density. The two ionisation chambers of the grid scanner are calibrated in respect of the particle count per supervising or monitoring unit of the ionisation chambers. The calibration is described by a calibration factor K, which depends on the irradiation energy E of the particles and the step width $\Delta x$ and $\Delta y$ of the grid scanner, that is to say, $K=K(E, \Delta x, y)$. The calibration of the ionisation chambers is carried out by a dose measurement in a homogeneously deflected irradiation field, wherein the discrepancies from the reference conditions are corrected and the display of the ionisation chamber is converted into an energy dose related to water $D_{scan}$. The calibration factor is calculated according to:

$$K(E, \Delta x, \Delta y)=(D_{scan}/M_1).\Delta x.\Delta y/(S(E)/\rho)$$

in which $(S(E)/\rho)$=mass stopping power of $^{12}C$ at an irradiation energy E, and M=monitoring units per coordinate point i of the ionisation chamber.

The relevant energy range (for example from 80 MeV/u to 430 MeV/u) is measured in a plurality of steps. The measurement site of the particular ionisation chamber checked is located in the isocentre 10, the ionisation chamber or the dosimeter being arranged in a solid-body phantom. The same table of the mass stopping power of $^{12}C$ is used as that on which the irradiation planning is based. In that manner, depending on the energy E and the step width $\Delta x, \Delta y$, a group of calibration factors K is obtained, the maximum permitted discrepancy from the reference values for each calibration factor being ±3%. From the group of calibration factors at least three values should be checked. In order to check consistency, this test procedure should be carried out daily.

The dose consistency must also be checked, since identical preselected monitoring units of the ionisation chambers must always result in identical dose displays. It is therefore recommended that the consistency of the dose be checked in the centre point of cubiform irradiation volumes, which are generated or scanned by the grid scanner or the magnets 13, 14 thereof, as a function of the group of calibration factors of the ionisation chambers. For that purpose, in order to obtain reference values the dose is measured in a phantom that is so positioned that the isocentre 10 is located precisely in the centre of its front face. In that arrangement, the irradiation is carried out inside an irradiation cube or dose cube with an edge of 5 cm length, the centre of which is arranged as measurement site at 11.3 cm water-equivalent depth. (The calculation of the control data for the generation of the dose cube is carried out by means of CT-based irradiation planning. For that step it is more advantageous to arrange the isocentre 10 on the site at which the beam enters the water phantom. Furthermore, the selected measurement depth renders possible standardisation of the measurement equipment for the different tests). The radiation dose determined in that manner is stored as a reference dose. The actual dose values measured subsequently can then be compared with that reference dose, the maximum permitted discrepancy between the actual and the nominal dose (reference dose) being ±3%. A daily consistency check should be carried out.

Also, the parameters influencing the particle count monitors and ionisation chambers need to be checked, there being checked in that procedure especially the dependency of the calibration factors K on the particle fluence and the particle flow. In both cases an annual consistency check should be carried out.

In order to check the dependency of the calibration factors on the particle fluence, the procedure carried out is essentially the same as for checking the consistency of the calibration factors. The measurements are carried out in a phantom, which with an area of 5×5 $cm^2$ is irradiated at energies of 150 MeV/u, 250 MeV/u and 350 MeV/u with the same beam intensity in each case. An ionisation chamber is arranged in the centre of the irradiated surface area. The monitoring values of the ionisation chamber are so laid down that a dose of 0.2 Gy, 0.5 Gy and 1 Gy, respectively, is produced at the measurement site. For those different monitoring values, concordance between the actual and the nominal dose is ascertained, a maximum discrepancy of ±3% being permitted. Adherence to that narrow tolerance is expedient and also practicable.

To check the dependency of the calibration factors on the particle flow, the procedure used is likewise substantially the same as that used to check the consistency of the calibration factors. In this case, however, the dose is kept constant and the beam intensity is in each case set at a high, a medium and a low value, so that concurrence of the actual radiation dose with the nominal reference dose can be checked for different intensities. In this case, too, a maximum discrepancy of ±3% is permissible.

Regarding the ionisation chambers and particle count monitors, the dependency of the calibration factors thereof on the beam position should be checked. Substantially the same procedure as that used to check the consistency of the calibration factors is carried out, but the arrangement employed is the same as that used in the above-described checking of the dose consistency. The measurements are carried out in an irradiation volume or irradiation cube of the grid scanner 13, 14 with an edge of 5 cm length, but with a lateral displacement of 2 cm and 6 cm. The monitoring values of the ionisation chambers are laid down such that a radiation dose of 1 Gy is produced in the centre of the irradiation volume. In checking the displays of the ionisation chambers, the value measured at the side should differ by no more than 3% from the value measured in the centre. In that case, too, an annual consistency check is recommended.

A further checking aspect of this checking section is concerned with the inspection of the dose distribution of the grid scanner 13, 14, in which both the depth distribution of the dose and the transverse distribution of the dose are examined.

The homogeneity of the depth distribution of the dose is checked as a function of a selected irradiation energy and selected monitoring values per irradiation energy value of the ionisation chambers used, since the depth dose homogeneity is crucially dependent on the energy selected and the consistency thereof. For that purpose, again parallelepipedal or cubic irradiation volumes are generated in a phantom with the grid scanner magnets 13, 14, wherein for each coordinate point of a layer (energy) a constant particle coverage, but a different particle coverage per layer, is used in such a manner that a homogeneous dose distribution is achieved in the irradiation cube. A plurality of dosimeters (ionisation chambers), for example 10 ionisation chambers, carry out measurements in different water-equivalent depths, the ionisation chambers being so positioned that irradiation of a plurality of ionisation chambers one behind another does not occur. The edge lengths of the irradiation cubes are, for example, 2.5 cm, 5 cm and 10 cm, the measurements of the ionisation chambers being carried out for depths of the centre points of the respective cube-shaped irradiation volume of 5 cm, 12.5 cm and 20 cm respectively. The monitoring values are established from the irradiation planning by a radiation dose, predetermined by the irradiation planning, being produced in the centre of the respective irradiation volume. By comparison of the actual measurement values with the reference values, the degree of variation of the displays of the ionisation chambers can be checked. A maximum discrepancy of ±5% can be tolerated. If that tolerance limit is exceeded, there must be a system intervention in order to correct the excessively large discrepancy. In order to check consistency, the above-described checking procedure should be carried out prior to each block of irradiation procedures.

The transverse distribution of the dose of the grid scanner is checked as a function of the energy in order to ensure that the homogeneity of the grid scan procedure is guaranteed at all irradiation energies used. In that case, when the ionisation chamber monitoring values are fixed and in each case irradiation energies are different (for example 100 MeV/u, 150 MeV/u, 200 MeV/u, 250 MeV/u, 300 MeV/u and 350 MeV/u) and beam fields are different, the radiation dose perpendicular to the direction of the beam is ascertained with a plurality of ionisation chambers measuring simultaneously. At the same time, open air in front of the dosimeters or ionisation chambers produces a blackening distribution on a verification film. With the grid scanner 13, 14, areas with a lateral face of, for example, 5 cm, 10 cm and 18 cm are produced, wherein the radiation dose should in each case be approximately 1 Gy. The standard deviation of the corrected displays of the ionisation chambers or of the verification film blackening inside the irradiation field is checked, the maximum tolerable departure from the reference values being ±5%. Non-tolerable departures from the reference values are corrected in order for adaptation to the measurement conditions that actually exist to be achieved. A consistency check should be carried out prior to each block of irradiation procedures, the use of the verification film with monitoring of the blackening of that verification film being sufficient in this case.

A further checking aspect of this checking section is concerned with the inspection of the field geometry in the grid scan procedure, the dependency of the spatial position of a particular irradiation volume of the grid scanner 13, 14 on selected irradiation energies being checked. For that purpose, cubic or parallelepipedal irradiation volumes are generated by the grid scanner 13, 14, wherein a constant particle coverage is used for each coordinate point of a layer (energy), but a different coverage is used per layer, such that a homogeneous dose distribution is obtained in the irradiation cube. Under those conditions a wedge-shaped solid-body phantom is irradiated, behind which a verification film is located. The position of the verification film blackening relative to the centre point of the irradiation is then determined.

In the measurement, the edge lengths of the irradiation fields are, for example, 4 cm, 7 cm and 12 cm, while the extent of the irradiation parallelepipeds or cubes in the direction of the beam is 2.5 cm, 5 cm and 10 cm. The measurements are carried out for water-equivalent depths of each of the centre points of the irradiation volumes of 5 cm, 12.5 cm and 20 cm respectively. The monitoring values of the dosimeters or ionisation chambers are so determined from the irradiation planning that a radiation dose predetermined by the irradiation planning is produced in the centre of the irradiation volume. There are defined as the field boundaries the locations at which the marginal fall-off in the blackening is 50% of the plateau value. The position of the distal field boundaries and of the lateral field boundaries viewed in the direction of the beam are examined and compared with reference values. A departure of 2 mm in each direction is tolerable, otherwise a correction of the system must be carried out in order to adapt the system to the measurement conditions actually existing. In order to check consistency, that checking procedure should be carried our prior to each block of irradiation procedures, a selection of in each case three conditions from the combinations of the above-described conditions being sufficient here.

Finally, a further checking aspect of this checking section is concerned with the verification of the overall system so as to be able to verify the accuracy of the applied radiation dose, in terms of its level and spatial dimensions, for each of the patients to be irradiated, so that a correct cooperation of the individual components of the system is ensured. In this procedure it is necessary to distinguish between the irradiation of a homogeneous medium and the irradiation of a non-homogeneous medium.

In the first case, as in the above-described verification of the concordance of calculated and measured dose distributions for a homogeneous medium, a homogenous phantom is used and essentially the same procedure is carried out, but with the exception that in this case individual patient irradiation plans are used as a basis. For all measurement points, the difference between the calculated radiation dose and the measured radiation dose is ascertained, and again an average discrepancy for all measurement points of 5% and a discrepancy for an individual measurement point of 7% is tolerable. In order to check consistency, this test should be carried out prior to each block of irradiation procedures.

In order to check the accuracy in the case of irradiation of a non-homogeneous medium that is to be irradiated, again a non-homogeneous phantom is used, wherein in this case irradiation planning is carried out by preparing only one hemispherical phantom from a solid, water-equivalent material having a radius of, for example, 8 cm. For irradiation planning, the centre point of the phantom is located in the isocentre 10 and the hemisphere of the phantom is opposite to the direction of irradiation. Various non-homogeneities, for example in the form of disks each having a diameter of 3 cm, can be inserted into the phantom, preference being given to the use of seven different materials or non-homogeneities having the following densities:

| No. | Density |
| --- | --- |
| 1 | 0.001 (air) |
| 2 | 0.30 (lungs) |
| 3 | 1.035 (bound water) |
| 4 | 0.92 (fat) |
| 5 | 1.05 (muscle) |
| 6 | 1.14 (soft bone) |
| 7 | 1.84 (hard bone) |

The planned target irradiation volume is, for three different directions of irradiation having an angle of irradiation of 0°, +45° and −45°, in each case a 2 cm-thick layer inside the hemi-spherical phantom, which directly adjoins the flat face of the hemisphere, so that the distal position of the irradiation volume coincides with the rear flat face. The homogeneous radiation dose planned in the target irradiation volume is 1 Gy. With those control data for controlling the grid scanner, the irradiation procedures are carried out with the three directions of irradiation, there being positioned both in the target irradiation volume and behind each non-homogeneity a dosimeter (that is, an ionisation chamber), the display of which is monitored. The ascertained energy dose at all of the measurement points inside the target irradiation volume should not exceed the threshold 1 Gy ±5%, whilst 5 cm behind the target irradiation volume the maximum tolerable departure from the calculated radiation dose relative to the target irradiation volume is ±10%. In addition, for all measurement points again an average discrepancy of the measured radiation dose of ±5% is tolerable, and for each individual measurement point a maximum discrepancy of ±7% is tolerable. In order to check consistency, this checking procedure should be carried out prior to each block of irradiation procedures.

What is claimed is:

1. Method for the verification of a calculated radiation dose of a heavy ion beam therapy system, wherein the heavy ion beam therapy system comprises:
at least one ion source (1) for heavy ions,
an accelerator device (2, 5) for the acceleration of the ions of the ion source (1) in the form of a treatment beam (11),
a beam guidance system (6, 8) to guide the treatment beam (11) from the accelerator device (2, 5) to at least one irradiation site for treatment of a patient, the beam guidance system (6, 8) comprising at least one beam guidance channel (6), and
a grid scanner device, arranged in the beam guidance system (6, 8), having a vertical deflection means (13) and horizontal deflection means (14) for the vertical and horizontal deflection of the treatment beam (11) perpendicular to its beam direction, with the result that the treatment beam (11) is deflected by the grid scanner device to an isocentre (10) of the irradiation site and scans a specific area surrounding the isocentre (10), and wherein irradiation is carried out on the basis of calculated radiation dose data and the accuracy of the calculation of the radiation dose data is verified by using a phantom with the aid of the following steps:

a) the radiation dose data are calculated for a plurality of specific measurement points in the phantom, b) irradiation of the phantom is carried out using the calculated radiation dose, and at the measurement points the radiation dose brought about there is measured, values ascertained by ionization chambers being converted into energy does values for verification of the calculated dose values, c) the discrepancy between the radiation dose calculated for the measurement points and the radiation dose measured for the measurement points is determined, and d) it is concluded that the accuracy of the calculation of the radiation dose data is adequate if the average discrepancy, for al the measurement points, between the calculated and the measured radiation dose values does not exceed a predetermined first tolerance value of ±5% and, for each individual measurement point, the discrepancy between the radiation dose calculated and measured for that measurement point does not exceed a predetermined second tolerance value of ±7%.

2. Method according to claim 1, wherein in step b) the radiation dose is measured with the aid of an appropriately positioned ionization chamber.

3. Method according to claim 1, wherein the accuracy of the calculation of the radiation dose data is verified, for a homogeneous medium to be irradiated, by using a water phantom.

4. Method according to claim 1, wherein the accuracy of the calculation of the radiation dose data is verified, for a non-homogeneous medium to be irradiated, by using a solid-body phantom having non-homogeneities.

5. Method according to claim 4, wherein the solid body phantom is spherical and consists of a water-equivalent material.

6. Method according to claim 4, wherein different non-homogeneities are interchangeably inserted in the solid-body phantom.

7. Method according to claim 4, wherein the steps a)–d) are carried out for at least three different non-homogeneity structures of the solid-body phantom, the first solid-body phantom having boundary layers between different materials, the second solid-body phantom having thin non-homogeneities and the third solid-body phantom having thick non-homogeneities.

8. Method according to claim 1, wherein the accuracy of the calculation of the radiation dose data is verified by using an irregularly shaped phantom.

9. Method according to claim 8, wherein the irregularly shaped phantom consists of a water-equivalent material and has the shape of a human head.

10. Method according to claim 1, wherein
a digital reconstruction of the phantom is calculated;
an image of the phantom is produced and compared with the calculated reconstructions to ascertain a discrepancy; and
it is concluded that there is an error in the calculation of the digital reconstructions if the discrepancy between the calculated reconstructions and the corresponding image exceeds a specific tolerance limit value.

11. Method according to claim 10, wherein a plurality of digital X-ray reconstructions of the phantom are calculated; and X-ray images of the phantom are produced from a plurality of imaging directions and individually compared with the corresponding X-ray reconstructions.

12. Method according to claim 10, wherein the tolerance limit value is 2 mm.

13. Method according to claim 1, wherein said heavy ions are carbon ions.

* * * * *